(12) United States Patent
Laufer et al.

(10) Patent No.: US 6,577,902 B1
(45) Date of Patent: Jun. 10, 2003

(54) DEVICE FOR SHAPING INFARCTED HEART TISSUE AND METHOD OF USING THE DEVICE

(75) Inventors: Michael D. Laufer, 3000 Sand Hill Rd., Building 4, Suite 100, Menlo Park, CA (US) 94025; Suresh K. Wadhwani, Mission Viejo, CA (US); Edward J. Nance, Corona, CA (US); Payam Adlparvar, Lake Forest, CA (US); Thomas F. Kordis, Rancho Santa Fe, CA (US)

(73) Assignees: Tony R. Brown, Anaheim, CA (US); Michael D. Laufer, Menlo Park, CA (US)

( * ) Notice: Subject to any disclaimer, the term of this patent is extended or adjusted under 35 U.S.C. 154(b) by 0 days.

(21) Appl. No.: 09/293,436

(22) Filed: Apr. 16, 1999

(51) Int. Cl.[7] .............................. A61F 7/00; A61B 18/04
(52) U.S. Cl. ...................... 607/102; 607/99; 607/113; 606/31
(58) Field of Search ......................... 607/99, 101, 102, 607/113, 115, 116, 119, 122, 154; 606/27–31, 32, 41, 42, 45, 48, 49, 50; 600/372–374, 393

(56) References Cited

U.S. PATENT DOCUMENTS 5,688,267 A * 11/1997 Panescu et al. ............... 606/41
5,693,078 A * 12/1997 Desai et al. ................. 607/102
6,029,091 A * 2/2000 de la Rama et al. ......... 607/102

\* cited by examiner

Primary Examiner—John P. Leubecker
(74) Attorney, Agent, or Firm—Burns, Doane, Swecker & Mathis, LLP

(57) ABSTRACT

A device and method for treating an infarct scar on a heart comprising an electric cable with proximal and distal ends; a handle with proximal and distal ends with the proximal end connected to the distal end of the cable; a stem with proximal and distal ends with the proximal end of the stem connected to the distal end of the handle; a heating element with a first surface for contacting infarct scar tissue connected to the distal end of the stem wherein the heating element comprises at least two electrodes and at least one temperature sensor positioned on the first surface for sensing a temperature of infarct scar tissue adjacent to the sensor; an energy source connected to the electrodes via the electric cable; and a regulator connected to the energy source and the temperature sensor of the infarct scar tissue, for controlling the temperature of the infarct scar tissue from about 60 degrees C. to about 99 degrees C. Once the heart has been treated, a restraint is disclosed that allows for the shrinkage to be maintained over time.

41 Claims, 9 Drawing Sheets

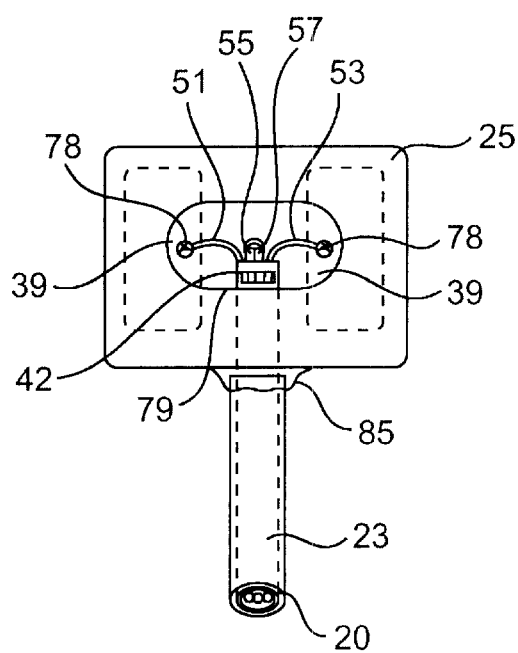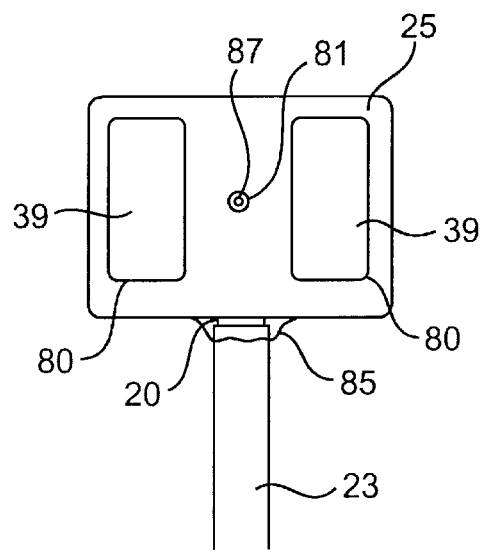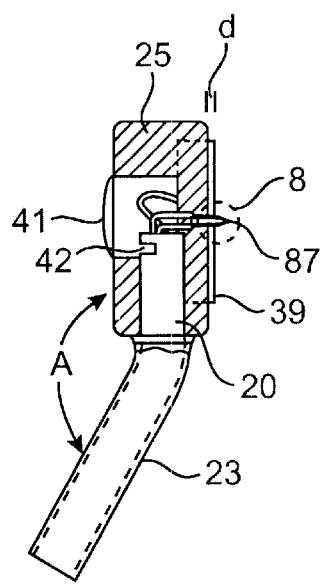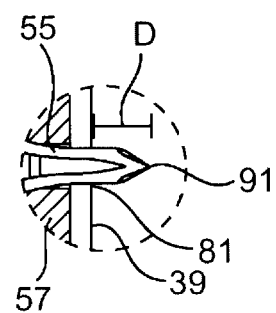
FIG. 5
FIG. 6
FIG. 7
FIG. 8

DEVICE FOR SHAPING INFARCTED HEART TISSUE AND METHOD OF USING THE DEVICE

FIELD OF THE INVENTION

The present invention relates generally to devices and methods that can deliver thermal energy to tissue. More particularly, the present invention is directed to devices and methods that can deliver thermal energy to an area of infarcted heart tissue which shrinks and thickens the infarcted area to thereby improve cardiac function.

BACKGROUND OF THE INVENTION

The mammalian heart has four chambers for receiving and pumping blood to various parts of the body. During normal operation of the heart, oxygen poor blood returning from the body enters the right atrium via the inferior vena cava, superior vena cava, coronary sinus, or the coronary veins. The right atrium fills and eventually contracts to expel the blood through the tricuspid valve and into the right ventricle. The right ventricle fills full of blood and then contracts beginning from the apex of the ventricle to the base of the ventricle and forces blood through the pulmonary valve to the pulmonary arteries and to the lungs. The blood becomes oxygenated at the lungs and then returns from the lungs to the left atrium via the pulmonary veins. The left atrium contracts to expel blood through the mitral valve and into the left ventricle. The left ventricle then fills full of blood and then contracts beginning from the apex of the ventricle to the base of the ventricle and forces blood through the aortic valve, into the aorta, and eventually to the body tissues.

The major blood supply to the heart is derived from the coronary arteries, two arteries that branch off from the aorta just distal from the aortic valve. The right coronary artery provides blood to the right side of the heart, the left coronary artery supplies blood to the left side of the heart including the left ventricle. Coronary artery disease usually affects the left coronary artery reducing the blood flow to the left ventricle. When the blood flow supplying oxygen and nutrients cannot meet the demands of the heart, the heart becomes ischemic and the patient usually suffers from chest pain (angina). When the flow of blood completely stops due to an occlusion of a coronary artery, the heart muscle becomes very ischemic and will die if blood flow is not restored in a few minutes.

A myocardial infarction occurs when the heart muscle cells die. The dead muscle cells are replaced by scar tissue over a period of a few weeks. The scar tissue is not contractile, therefore it does not contribute to the pumping ability of the heart. In addition, scar tissue is somewhat elastic which further reduces the efficiency of the heart because a portion of the force created by the remaining healthy muscle bulges out of the scarred tissue (i.e., ventricular aneurysm) instead of pumping the blood out of the heart.

If the myocardial infarction is fairly large, the scar tissue will form across the width of the heart and is described as a transmural infarct. The scar tissue will be present both at the endocardial side (inside of the heart) and the epicardial side (outside of the heart). Transmural infarcts are typically indicated when a patient has a Q-wave infarct as diagnosed on an electrocardiogram (ECG).

Transmural infarcts can lead to congestive heart failure, a condition where the heart cannot pump enough blood to the body to maintain the supply of oxygen and nutrients to keep up with the demand. Congestive heart failure is generally treated with lots of rest, low salt diet, and medications such as angiotensin converting enzyme (ACE) inhibitors, digitalis, vasodilators, and diuretics. In some myocardial infarcts the infarct is surgically removed (an infarctectomy or an aneurysmectomy) and the healthy heart is sutured together. This treatment is very invasive and has a high morbidity and mortality rate. Ultimately, most patients with congestive heart failure die of the condition or are given a heart transplant.

The scar that forms in the myocardium is primarily composed of collagen. Collagen demonstrates several unique characteristics not found in other tissues, Intermolecular cross-links provide collagen with unique physical properties of high tensile strength and substantial elasticity. The cross-links in collagen are organized such that the three dimensional protein structure of natural collagen forms into a rope like structure with striations along the rope. When collagen is heated to temperatures above about 60 to 65 degrees centigrade, it is believed that the cross-links rupture and the protein becomes more globular and less rope like. As the collagen becomes more globular, the collagen shrinks along its axial length. The higher the temperature the collagen is heated, the more globular the collagen becomes and the greater the shrinkage. Collagen can shrink to almost about ½ of its original length. The caliber of the collagen fibers also increasers as collagen is heated, up to a four fold increase depending on the temperature.

In a previously filed U.S. Pat. No. 6,071,303 issued Jun. 6, 2000 Michael D. Laufer disclosed the use of heat to treat infarcted heart tissue, the disclosure of which is hereby incorporated by reference. The heat would shrink the collagen containing tissue and increase the pumping efficiency of the heart by decreasing the area that was not pumping efficiently. In the Laufer application, it is disclosed that the scar tissue is to be heated to certain temperature ranges, however, it does not disclose specific means to control the temperature to the desired range. Additionally, the application did not disclose a specific device heating element configuration to optimize infarct scar heating throughout the scar.

Animal studies also show that heating the scar tissue to shrink the collagen gave vary good initial clinical results, however, chronically the body replaced the denatured collagen with normal collagen and the scar tissue dilated such that the acute results were not maintained.

What is needed therefore is a device and method for heating myocardial scar tissue and controlling the temperature of the tissue to a set temperature range and an optimal heating element to throughly heat the infarct scar. What is also needed is a device and method that maintains the improvement in cardiac function chronically.

SUMMARY OF THE INVENTION

The present invention provides a device and method for treating a myocardial infarction. The present invention is a device for controllably heating an infarct scar. One embodiment is a bipolar radio frequency (RF) device comprising an electric cable with proximal and distal ends; a handle with proximal and distal ends with the proximal end connected to the distal end of the cable; a stem with proximal and distal ends with the proximal end of the stem connected to the distal end of the handle; a heating element with a first surface for contacting infarct scar tissue connected to the distal end of the stem wherein the heating element comprises at least two electrodes and at least one temperature sensor positioned on the first surface for sensing a temperature of infarct scar tissue adjacent to the sensor; a radio frequency energy source connected to the electrodes via the electric cable; and a regulator connected to the energy source and the temperature sensor of the infarct scar tissue, for controlling the temperature of the infarct scar tissue from about 60 degrees C. to about 99 degrees C.

A further embodiment illustrates that the electrodes have a length L, a width W, and are separated by a space S wherein the space S is less than 2 times the length L and no greater than 10 mm, the width W of the electrodes is greater than 0.2 times the space S and equal or less than the length L. This.electrode configuration optimizes the treatment area.

Yet another embodiment illustrates a heating element and a temperature sensor that protrudes from the surface of the heating element. The temperature sensor accurately measures the temperature of the adjacent tissue and also serves as an anchor to secure the heating element on a beating heart.

Finally, once the infarct scar tissue has been treated, a reinforcement patch material is secured over the scar to maintain the new geometry of the heart chronically.

The device is used on an infarct scar that has been surgically identified and isolated. The device is placed on the scar and a temperature sensor controls the amount of energy used to heat the scar tissue to a predetermined set point ranging from about 60 degrees C. to about 99 degrees C. The heat is applied for about 5 to about 60 seconds until the area under the device has shrunk. The device is then moved to other areas of the scar until the entire scar tissue has been shrunk. Then a reinforcement patch material is secured over the heat treated infarcted scar tissue to prevent dilation during the bodies healing process.

The present invention provides advantages of thoroughly heating an infarct scar, controlling the temperature of the scar, and maintaining the improved cardiac function over time.

BRIEF DESCRIPTION OF THE DRAWINGS

As used herein, like reference numeral will designate similar elements in the various embodiments of the present invention wherein:

FIG. 5 is a schematic top view of the distal end of the heating device;

FIG. 6 is a bottom view of the heating device;

FIG. 7 is a schematic side cross-sectional view of the heating device;

FIG. 8 is an enlarged view of the temperature monitoring means in circle 8 of FIG. 7;

DETAILED DESCRIPTION OF THE PREFERRED EMBODIMENTS

Figure 1:
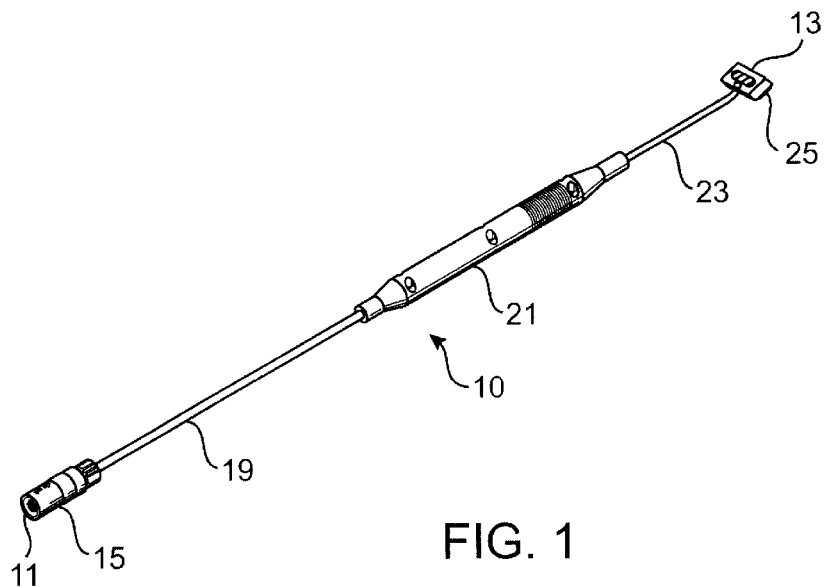
FIG. 1 is a plan view of a heating device that can deliver radio frequency energy and monitor temperature.

The present invention provides a device and method for heating myocardial scar tissue to a desired temperature and controlling the device to maintain that temperature for a desired period of time. Turning now to FIG. 1, one embodiment of the heating device 10 is generally illustrated. The heating device has a proximal end 11 and a distal end 13.

At the proximal end is provided a connector 15 that can be used to connect to a power supply or an extension cable. A flexible electrical cord 19 is connected to the connector at one end. At the other end of the cord is a handle 21 for holding and using the device. Connected to the proximal end of the handle is a stem 23 which spans from the handle to the heat delivering member 25.

Figure 2:
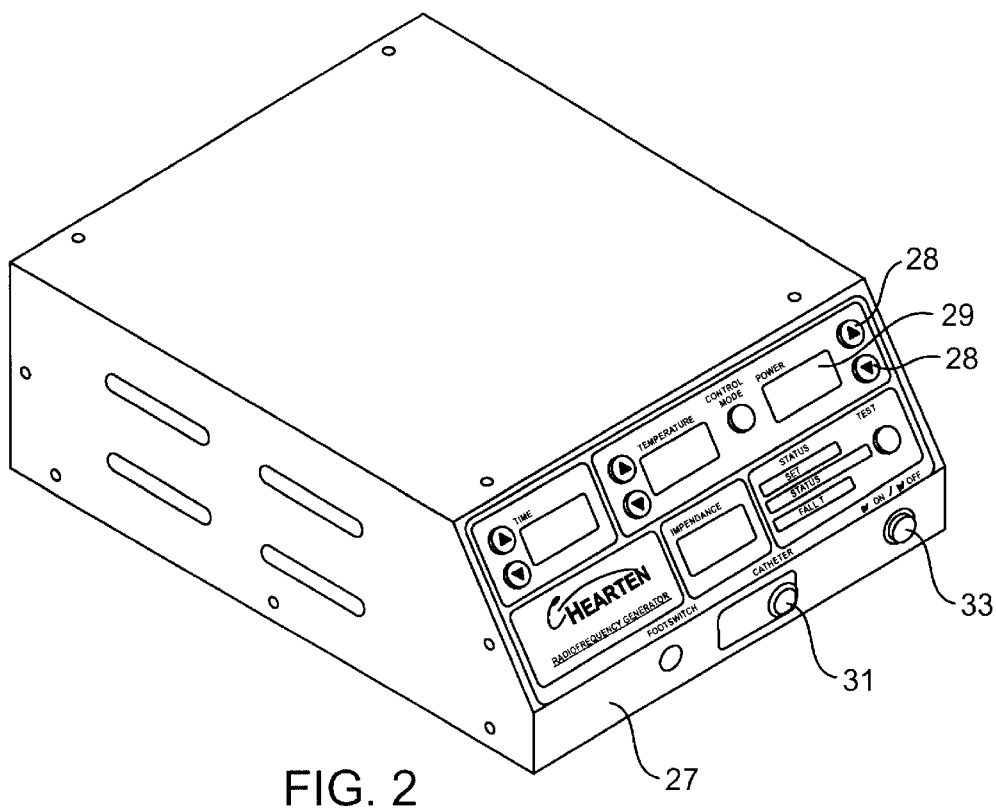
FIG. 2 is a plan view of a radio frequency generator and controller.

FIG. 2 illustrates a controller box 27 that supplies power to the heating device. The controller box is connected to a standard electrical outlet and delivers power to the heating device. The controller box is provided with a display 29 that shows the power settings, duration of the power and the temperature the device is to be controlled to. The time duration, temperature, and maximum power to be used is controlled by the operator of the device and are adjusted via controllers 28 on the controlling box. The box is also provided with a standard on/off switch 33 and a connection port 31 for connecting the heating device to the box.

In the preferred embodiment, the controller box generates standard radio frequency electrical energy for delivery via the delivering member of the heating device. Radio frequency generators are commercially available from numerous manufacturers, Stellartech Research Corporation in Mountain View, Calif. being one. The controller box can generate from about 0.2 watts to 100 watts of power at a frequency ranging from about 1 kHz to about 1000 kHz with 460 kHz being presently preferred. The time duration for the radio frequency generator can be adjusted from about 1 sec to about 300 seconds, with a time duration of about 25 to about 60 seconds being presently preferred. Although the controller box in the illustrated embodiment is generates RF energy and controls the RF energy, these functions could be split over different devices such as an RF generator being controlled by a separate microprocessor.

The operator of the controller box sets the temperature point, the maximum power to be delivered, and the duration of the power delivery. When the operator of the controller box connects the device and turns the power on to the device, the box delivers the maximum power to the device until the temperature is reached. Then controller then reduced the power to maintain the temperature and controls the amount of power being delivered based on the temperature. The temperature set point can be varied from about 60 degrees C. to about 100 degrees C., with a range from about 65 degrees C. to about 95 degrees C. being presently preferred. As described below, the depth of treatment can be controlled by properly selecting the time and temperature of the treatment with properly spaced electrodes.

Figure 3:
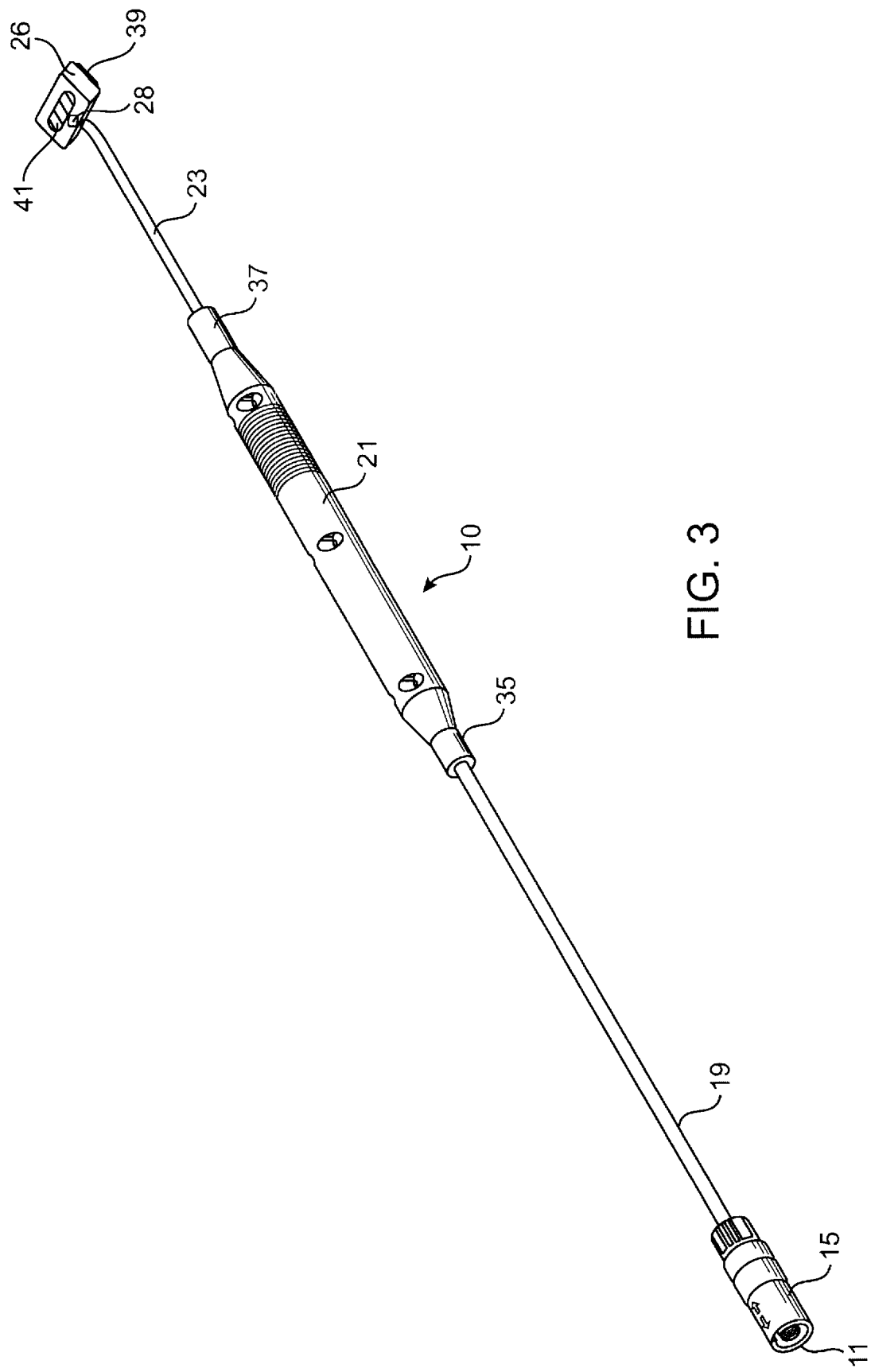
FIG. 3 is an enlarged plan view of the heating device of FIG. 1.
Figure 4:
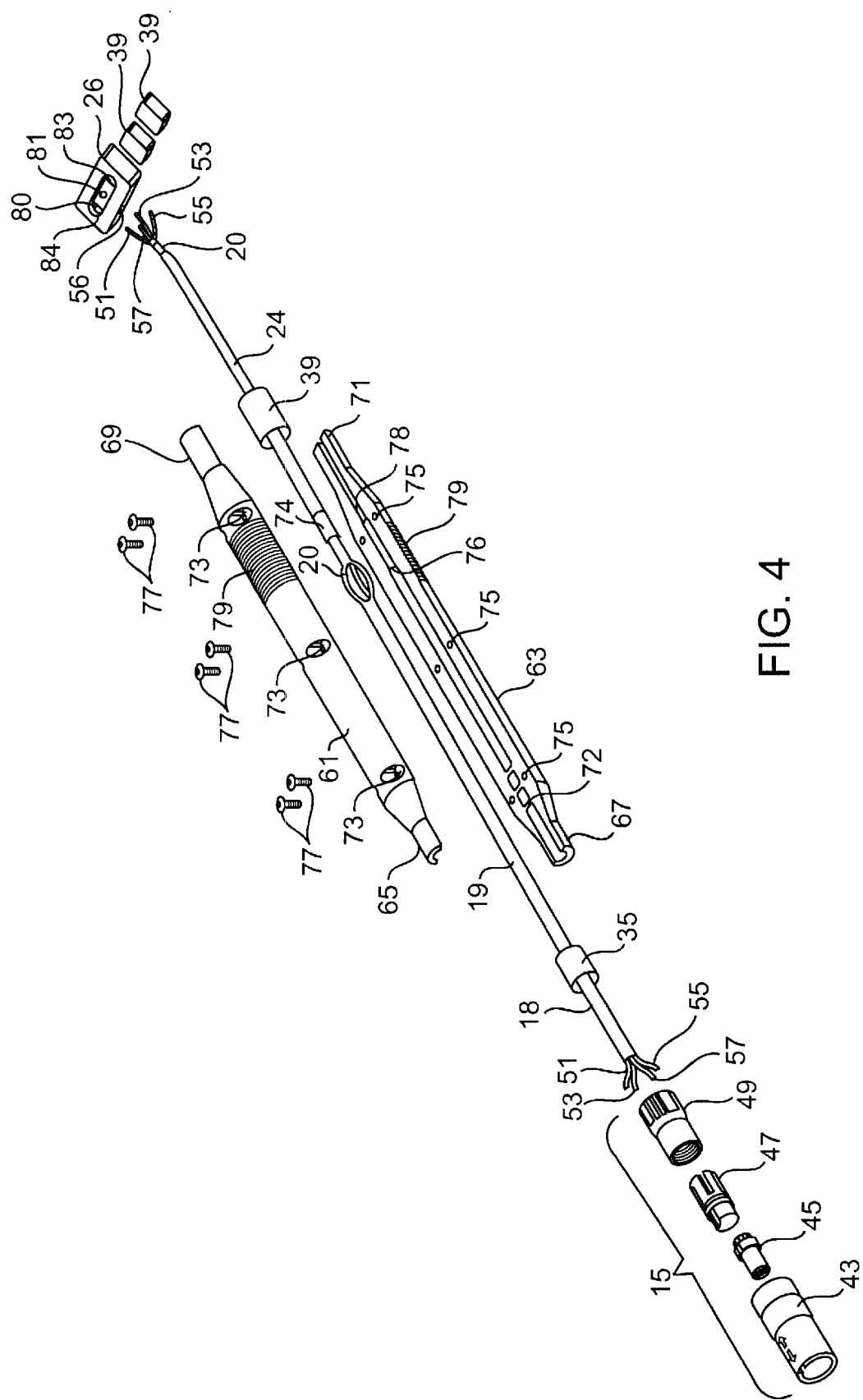
FIG. 4 is an exploded view of the heating device of FIG. 1.

Turning now to FIGS. 3 and 4, the device 10 is further illustrated. Starting at the proximal end 11, the device comprises an electrical connector 15 such that the device can be connected to a suitable cable or can be connected directly to the controller box. The preferred connector actually comprises four components, an outer proximal housing 43, a multipin solderable connector 45 for attaching the wires from the cable, a fitting 47 for stabilizing the multipin connector, and an outer distal housing 49 that mates with the outer proximal housing. Other standard connectors besides the one illustrated could also be used.

The cable 19 is provided with a plurality of wires. In the present embodiment four wires, 51, 53, 55, and 57 are used. The wires are insulated from one another and the insulation on the distal ends are stripped for soldering into the multipin connector. The wires provide for electrical connection from the connector to the heat delivering member and temperature sensor. The cable is also provided with an outer sheath 18 that is insulated.

The cable spans from the connector to the handle 21. In the preferred embodiment, the handle comprises two halves, a top half 61 and a bottom half 63. The axial center of the handle halves has a hollow core 70 to allow for the cable to fit inside the handle. The core's diameter is reduced near the distal end of the handle to form a smaller channel 76. The reduction in the diameter of the hollow core corresponds to the distal end of the cable sheath. At the proximal end of the hollow core, there are provided indents 72 that when the top half and the bottom half are fitted together, the indents slightly deform the cable and prevent the cable from rotating or from pulling out of the handle. Also provided near the distal end of the handle in the hollowed out portion is a flat channel 78 which as described below secures the stem 23 of the device inside the handle. The cable is secured by a friction fit within the handle. It is to be noted that the cable could also be fixed within the handle by other means well known in the art such as adhesives, welds, or the like.

The handle is provided with a plurality of holes 73 and threaded holes 75 that mate with screws 77. The screws are used to secure the top and bottom halves of the handle together. The handle is also provided with two ring members 35 and 39 which fit over the proximal end 67 and the distal end 71 respectively when the two handle haves are fitted together. These rings also secure the two handle haves. Finally, the handle is provided with ribbing 79 to help the health care practitioner hold the handle while using the device. Although the handle as illustrated comprises two halves that fit together, the handle could be injection molded using standard molding materials and techniques and formed as one singular unit with the components of the handle sealed within the injection molding material.

Turning now to the stem 23, the stem is hollow and fairly sturdy. The stem can be made from numerous materials such as a metal hypotube and the like, or it can be made from plastics. A thin hollow heat shrinking tube 24 is fitted outside the stem and electrically insulates the stem from the operator of the device. The insulating tube can be made from numerous materials, polyolefin being currently preferred. The stem is flat crimped near the proximal end such that the flat crimp 74 fits into the flat channel 78 of the handle. The flat channel is not as deep as the narrow channel and prevents the stem from turning inside the channel or from being pulled out of the channel.

At the distal end of the stem is the heat delivering member which in the illustrated embodiment comprises an electrode housing 26 and a plurality of electrodes 39. The distal end of the stem fits into a side hole 56 in the housing. The stem is angled with an angle A that ranges from about 120 degrees to about 180 degrees with 160 degrees being presently preferred. At the distal end of the stem is a notch 42 that anchors the stem inside the housing when a sealing material 41 is used to seal the housing and the wires inside the housing as discussed below. Optionally, a display signal 28 such as an LED can be used to give visual feedback of when the device has RF current going through the device. Such display signal would be electronically connected to the controller box and would give a visual display when the controller was delivering energy to the electrodes.

Turning now to FIGS. 4–8, the housing has a top opening 84 and a plurality of bottom openings 80 that correspond to the electrodes. Also provided in the housing is a side opening 56 for the stem 20 to be inserted. Once the stem is inserted and the electrical connections are made, the stem is secured with an insulating glue 85 such as polyurethane and the like.

In the preferred embodiment, there are two electrodes 39 and the size of the openings are just larger than the electrodes to make a snug fit. Once the electrodes are placed in the housing, the exposed surface of the electrodes project a distance d from the bottom of the housing. The distance d can vary from about 0.01 mm to about 1 mm with about 0.1 mm being presently preferred. Two wires, 51 and 53, from the cable 19 are electrically connected to the electrodes via solder connection 78. The top opening 84 is large enough to provide room for electrically connecting each wire with an electrode. Once the electrodes and wires are in place the top opening is sealed with sealing material 41 such as polyurethane and the like. The stem is notch so that the sealing material can wick inside the stem and help bond the stem inside the housing.

Alternately, the electrodes could be plated onto the housing instead of being fitted into the housing. It is very important that the electrodes have a smooth surface without any sharp edges or corners. If there are sharp edges or corners, these serve as current risers where the RF current from the RF generator will collect and cause non-uniform heating within the scar tissue. In the presently preferred embodiment the electrodes have rounded corners and edges and are polished in a water/rock tumbler to insurer that the edges are smooth and free of any burrs or other rough spots. One of ordinary skill in the art could use different techniques to create the electrodes, however the electrode placement and location is critical to having a good result as described below.

In the center of the housing is a small hole 81 for a standard temperature sensing lead. In the preferred embodiment the temperature sensing lead consists of two different wires 55 and 57 which form a temperature sensor 87 (see FIGS. 6–8). The temperature sensing lead wires are threaded through the side opening 56 and down the central opening 81 to project from the bottom surface of the housing. In the illustrated embodiment the twisted wires form a thermocouple and have a sharp tip 97 for placement into the tissue to be treated. Other temperature sensors could also be used such as a thermistor or the like. The temperature sensor projects a distance D from the surface to measure the temperature of the tissue being treated. The distance D can vary from about 0.1 mm to about 10 mm with a range from about 1 mm to about 2 mm being preferred. The most preferred distance is 1.25 mm. The sharp tip and distance D allows the temperature sensor to be placed within the actual scar tissue being heated to measure the tissue that is adjacent to the temperature sensor. Additionally, if the distance D is between 1 and 2 mm and the temperature sensor is centered about half-way between the two electrodes as illustrated, then the thermocouple will measure the tissue at its hottest point. This is due to the fact that the RF energy being delivered will have the highest current density, and hence tissue temperature, about 1 to 2 mm into the tissue if the electrode spacing is appropriate, see discussion below. Another benefit of having the temperature sensor project from the surface of the holder is to have the sensor serve as an anchor to the device when the device is used on a beating heart. The temperature sensor will pierce the infarcted heart tissue and keep the heating element and the electrode in contact with the infarcted scar tissue.

When the heating device is used, the temperature of the tissue at the temperature sensor can be controlled to a specified temperature range by adjusting the power of the RF energy being delivered to the electrodes through a temperature control feedback loop. Once the temperature sensor is measuring the desired temperature (85 degrees C. for example) then the amount of RF energy being delivered to the electrodes is reduced to a level which maintains the temperature instead of continuing to heat the tissue to a higher temperature.

Figure 9:
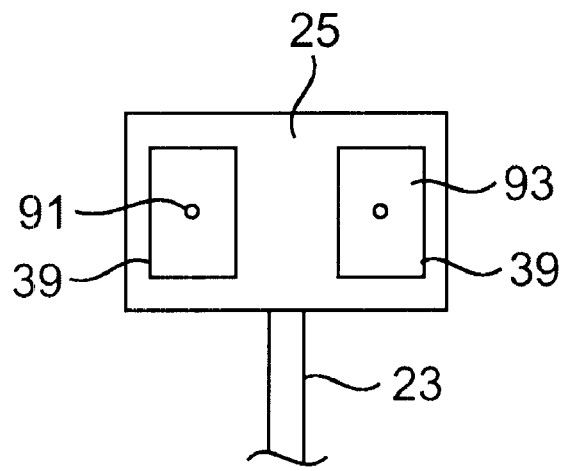
FIG. 9 is a schematic view of an alternate embodiment of the heating device.

Although the preferred embodiment has a single temperature sensor that protrudes from the bottom surface of the housing, FIG. 9 illustrates an alternate embodiment where there are two different temperature sensors, 91 and 93 on the exposed surface of the electrodes. The temperature sensors are located within the electrodes by drilling a hole in the electrodes and placing the sensors within the hole. The holes are then filled with a potting material such as polyurethane and the like. Lead wires are electrically connected to the sensors for connecting to the generator/controller. In the preferred embodiment the sensors are thermocouples that are made out of the lead wires, although other sensors could be used such as thermistors. In this embodiment, the temperature of the tissue adjacent to the electrodes are monitored and can be appropriately controlled.

Another aspect of the invention is the size and spacing between the electrodes. It is desirable to have as uniform heating through the infarct scar as possible between the electrodes as possible. In order to have uniform heating, there needs to be a certain current density through the tissue and a certain area of the electrodes. Additionally, the electrodes need to be spaced apart a set length to have the best effect. If the electrodes are too close, the tissue heating occurs primarily on the surface of the tissue adjacent to the electrodes. Tissue located deep under the electrodes do not heat up as well since very little current is traveling through the deep tissue. If the electrodes are spaced too far apart, then the electrodes act much more like two separate unipolar electrodes and the heating only occurs right near the edges of the electrodes. The reason for this type of heating pattern is that there is too much tissue between the electrodes and the current density goes down as the current finds many different pathways between the electrodes. Increasing the power being delivered to the electrodes does not help because then the temperature near the edges of the electrodes will get too hot and will singe the tissue. Singed tissue is dehydrated and acts like an insulator and prevents current from traveling through the tissue.

Figure 10:
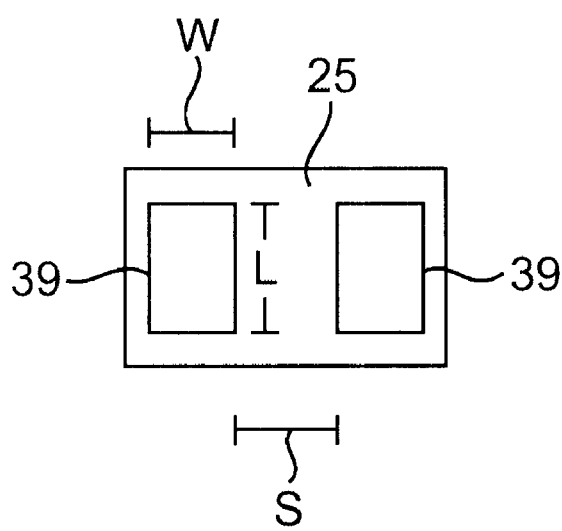
FIG. 10 is a schematic view of the critical dimensions of the electrodes within the heating device.

Turning now to FIG. 10, a schematic illustration of the heating element 25 is shown where the electrodes 39 have a length L, width W and are separated by a space between them S. The space S should be no longer than 2 times the length L. Preferably the space S should be no longer than the length L and more preferably range from about 0.3 L to about 1 L, with 0.625 L being presently preferred. The space S should be no greater than 10 mm, more preferably less than 6 mm. If the device is used on small mammals, i.e. rats, mice and the like, the space S should be less than 3 mm with the width W of each electrode being 2 mm yielding at least a 5 mm heat treatment x\zone as described below. If the device is used on larger mammals, i.e. humans, sheep, and the like, the space S should be no greater then 8 mm. Currently 5 mm space is used for heating devices that can treat larger mammals. The width of the electrodes can vary, but should be no smaller than 0.2 times the space S. Currently, the preferred width ranges from about 0.2 S to about 2 S, more preferably 0.33 S to about 1 S, with 0.8 S being presently preferred. The width W should be equal or less than the length L. Currently the preferred width ranges from about 0.2 L to about 1 L, more preferably 0.33 L to about 0.67 L, with 0.5 L being presently preferred. Thus, the presently preferred electrode configuration is for the electrodes to have a length L of 8 mm, a width W of 4 mm, and a spacing S of 5 mm. The electrodes also have a thickness which is not illustrated. The thickness of the electrodes should be as thin as possible but sufficient enough to deliver RF energy without heating because thick electrodes do not heat up and are actually a heat sink taking heat away from the tissue. Currently the thickness of the electrodes is between 0.1 mm and 4 mm, with 1.5 mm thickness being presently preferred.

Figure 11:
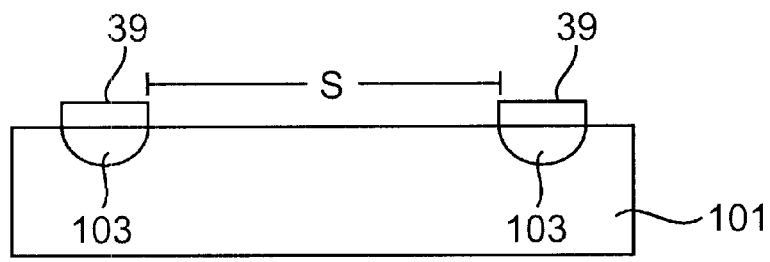
FIG. 11 is a schematic view of the heating zone created by widely spaced electrodes.
Figure 12:
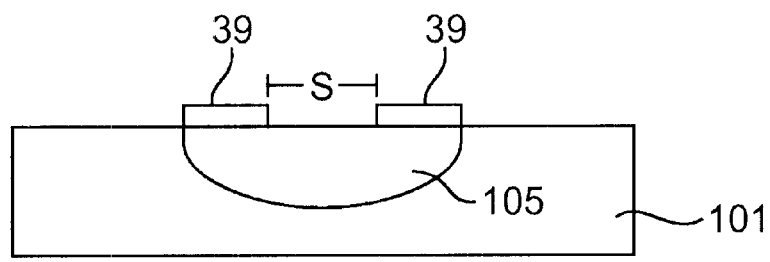
FIG. 12 is a schematic view of the heating zone created by properly spaced electrodes.
Figure 13:
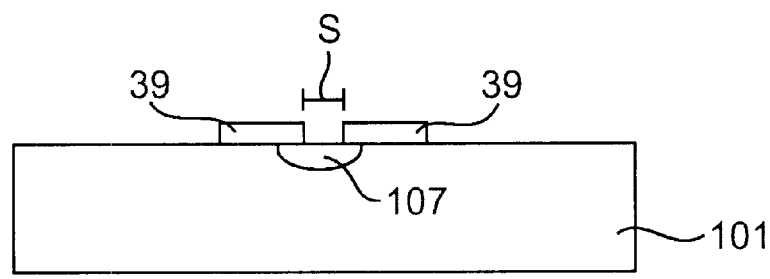
FIG. 13 is a schematic view of the heating zone created by too closely spaced electrodes.

FIGS. 11–13 schematically illustrate the effect of spacing and the zone of tissue heating. In FIG. 11, the electrodes 39 are spaced too far apart (greater than 10 mm) and the heating zones 103 created in the tissue 101 are small and widely separated. FIG. 12 illustrates electrodes that are properly spaced and create one heating zone 105 in the tissue that penetrates fairly deep into the tissue. In small mammals, the treatment zone will laterally range from about 5 mm to about 8 mm, and will penetrate about 1 mm deep, in large mammals, the treatment zone will laterally range from about 8 mm to about 15 mm, and will penetrate about 1 to about 3 mm deep. FIG. 13 illustrates electrodes that are too close to each other. One small heating zone 107 is created that does not penetrate deep into the tissue. Presently, using the preferred electrode spacing and dimensions listed above, the temperature of the tissue being treated can become greater than about 65 degrees C. (the shrinking point of collagen) to a depth of about 3 mm in a 5 mm infarct scar using the temperature set point of 95 degrees C. and heating for about 40 seconds. Setting the temperature set point to 90 degrees C. and treating for 40 seconds can treat to a depth of about 2 mm. Setting the temperature set point to 85 degrees C. and treating for 35 seconds can treat to a depth of about 1 mm. Thus, depending on the thickness of the infarct scar, the temperature can be adequately controlled. The heating zone profiles are ideal for treating infarct scar tissue on a beating heart in that the endocardial tissue is kept at body temperature reducing the risk of thrombosis and embolisms.

Other forms of energy delivery do not as readily provide a controllable heating zone as the present device. For example, laser energy could be used to heat an infarct scar, however the heat would only be generated at the surface of the heart and would have to conduct through the heart tissue. To generate a deep heating zone, the surface of the heart would probably have to be heated higher than 100 degrees C. which can cause undue desication and damage to the scar tissue. Resistive heating or applying a hot surface to the scar again would only treat the outermost area of the scar and would be difficult to treat the tissue deeply. Microwave energy radiates from an antenna and would tend to be more difficult to control and increase the risk of enocardial thrombosis.

Figure 14:
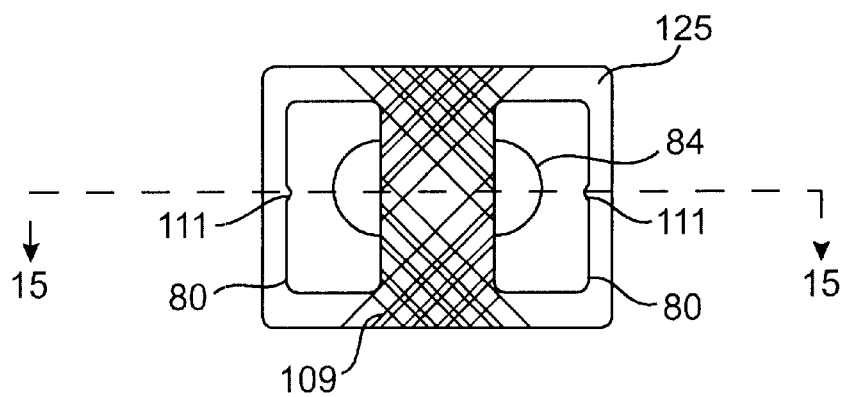
FIG. 14 is a bottom view of an alternate electrode housing.
Figure 15:
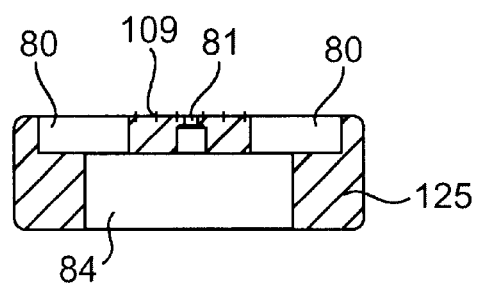
FIG. 15 is a cross-sectional view of the electrode housing of FIG. 14 taken along line 15—15.
Figure 16:
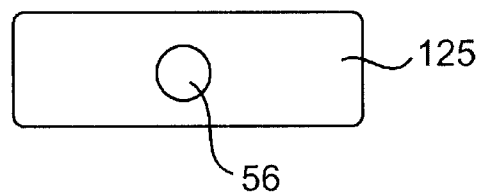
FIG. 16 is a side view of the electrode housing of FIG. 14.

FIGS. 14–16 illustrate a further embodiment of an electrode holder 125. In this embodiment the electrode holder has a plurality of grooves 109 on the bottom surface that will come into contact with the tissue to be treated. The grooves, along with the temperature sensor as described above, help to stabilize the device on a beating heart by increasing the friction between the electrode housing and the tissue being treated. This embodiment, the housing is injection molded using electrically insulating polycarbonate and then the grooves are machined onto the surface. Other material besides poly carbonate can be used such as polysulphone and the like. Additionally. The lateral sides of the electrode openings 80 have a projection 111 for stabilizing the electrodes once they are in place. The other reference numbers in FIGS. 14–16 correspond to similar components of electrode housing 26 described above.

Figure 17:
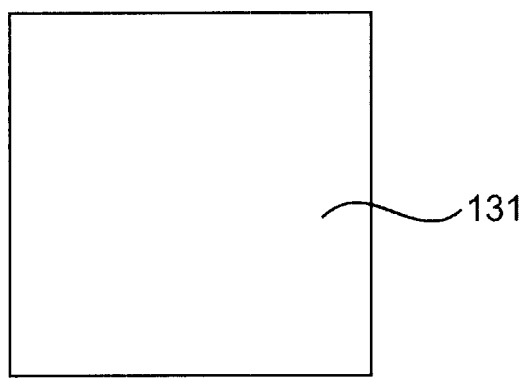
FIG. 17 is a top view of a restraint.

FIG. 17 illustrates a restraint used in the present invention. The restraint is used to prevent loss of the infarct scar reduction over time. The restraint in the presently preferred embodiment is a woven polyester material that is 10 cm by 10 cm. However, other restraints could be used such as the patient's pericardium or other autologous connective tissue such as fascia lata, bioabsorbable materials, biodegradable materials, polytetraflouroethylene (PTFE), polypropylene, polyethylene, polyurethane, and other materials well known in the synthetic medical fabric device industry.

Figure 18:
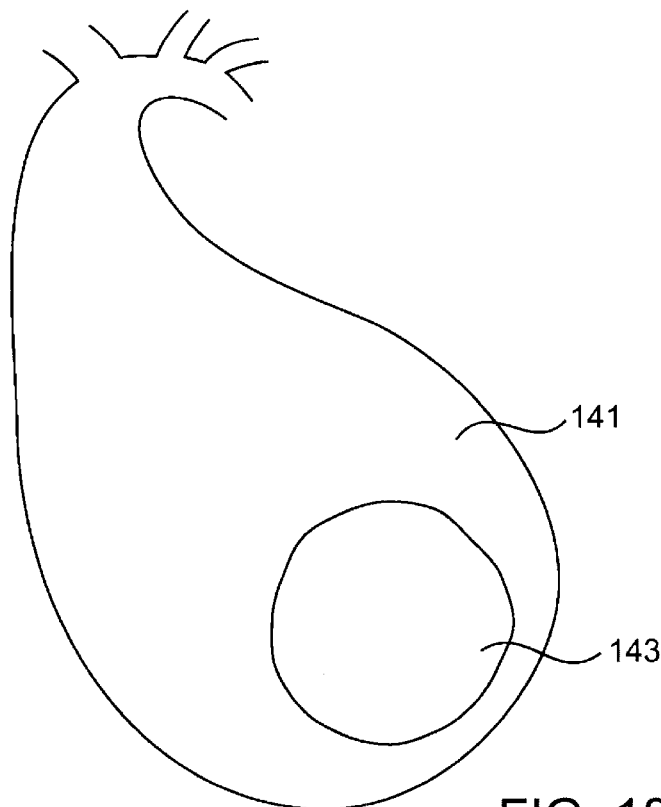
FIG. 18 is a schematic view of an infarcted heart.
Figure 19:
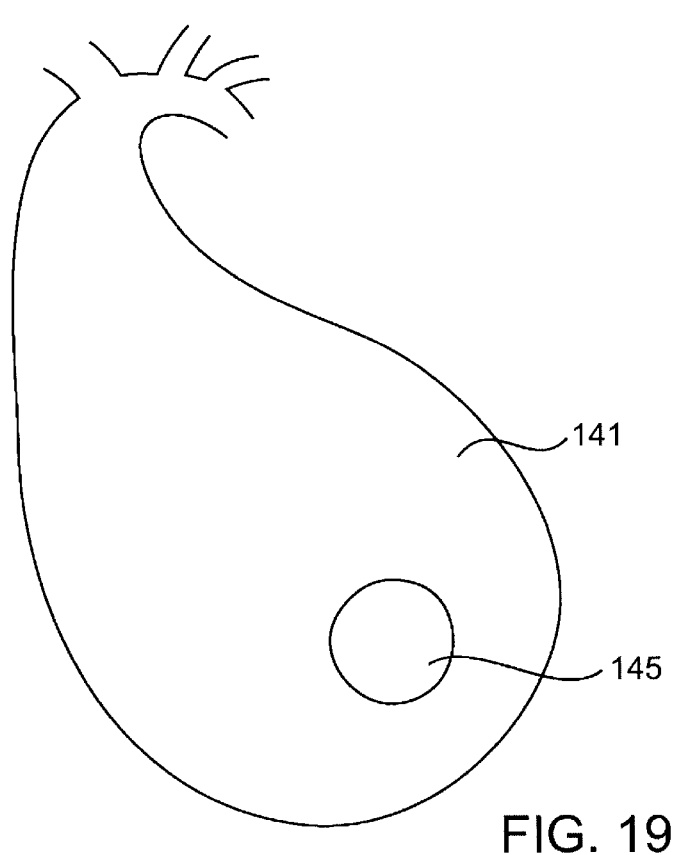
FIG. 19 is a schematic view of the infarcted heart of FIG. 18 after heat treatment.

FIG. 18 schematically illustrates a heart 141 with an infarcted zone 143. After the treatment, the treated infarcted zone 145 (see FIG. 19) is dramatically reduced in area. Finally, the restraint is secured onto the heart with tack sutures 151 and running sutures 153. Alternatively, the restraint could be adhered to the heart using tissue adhesives such as cyanoacrylate, fibrinogen glue, and the like.

The heating device is used in the following manner. First a mammal with a myocardial infarction is evaluated to ensure that the infarct area is stable and has minimal inflamation. This occurs after at least 4 weeks past the onset of the infarction and may last as long as about 12 weeks depending on the mammal to be treated. In humans, at lease 6 to 8 weeks post acute myocardial infarction is needed to reduce the inflamation. The evaluation can include ECG, stress ECG, cardiac imaging (angiography, ventriculography, echocardiography, fluoroscopy, MRI, nuclear medicine scans, and the like) functional testing and other standard medical cardiovascular evaluations. Once a proper patient is identified, the patient is prepared for surgery.

In the operating room, the patient's chest is incised and the heart is exposed. It is contemplated that the chest incision can range from a small minimally invasive incision to a full sternotomy. Once the heart is exposed the area of infarction is identified. The infarcted area does not contract like the normal heart muscle. It may contract less (hypokinetic) not contract at all (akinetic) or even bulge out when the rest of the heart contracts (dyskinetic). Additionally, the infarct is a different color and texture than the rest of the heart. The infarct, being mainly made up of collagen, is whiter and stiffer than the normal muscle of the heart which is red and contractile. If the infarct is covered by adipose tissue, the adipose tissue is removed by standard surgical means.

It is contemplated that the present invention would be used on the heart while the heart is beating. This way the patient has less chance of having complications from the operation since the patient will not be on heart-lung bypass. However, if the situation dictates, the present invention can be used on a patient that is on heart-lung bypass by carefully regulating the set point for the temperature sensor and the amount of time for the treatment.

After the heart is exposed, the heating device is placed on the infarcted area. RF energy is then delivered to the device via the radio frequency generator/controller. The RF energy is delivered to heat the infarcted tissue to a temperature greater than 60 degrees C., preferably greater than 65 degrees C., but less than 100 degrees C. If the tissue is heated to greater than 100 degrees C. for any length of time, the tissue may dessicate and char, which then insulates the surrounding tissue from the RF current and prevents good heating. In the present embodiment, if the temperature sensor measures a temperature of 102 degrees C. or greater for two seconds it will automatically shut off. Preferably RF energy is delivered from about 0.2 watts to 100 watts of power, at a frequency ranging from about 1 kHz to about 1000 kHz, for about 1 second to about 300 seconds. In the current preferred method, up to 20 watts of power can be delivered to have the tissue reach a temperature near the temperature sensors between about 65 and 95 degrees C., with set points of 85, 90 and 95 degrees C. being presently preferred. The frequency used is about 460 Khz and usually 30 to 40 seconds per treatment is used to ensure a good depth of the heat zone created.

When the collagen reaches a temperature above its glass transition point, the collagen denatures and changes shape from a long linear protein to a globular protein. This change in shape causes the collagen in the infarct to shrink. Once some of the collagen has shrunk, more collagen is now being exposed to the RF energy and being heated and more collagen will shrink. Eventually a steady state is reached where no further collagen will shrink based on the location of the heating element. This usually occurs within 20 to 40 seconds. Once this occurs, the heating element is moved to another area of the infarct that has not been treated and RF energy is applied to this area. In the preferred method, the infarct scar is treated in the center of the scar first. After the first treatment, the heating device is moved in a tiling direction from the center, overlaying only a small area that has been treated and working to the edges of the scar. Once the entire infarcted area is treated any areas that appear to need further treatment are retreated to ensure that the entire infarcted area was treated. Care is taken to not treat healthy contracting myocardium in that the treatment could injure healthy myocytes.

Once the device has been properly used, the treated and altered infarct is about one half the size of the original infarct. This reduction in the surface area of the infarct reduces the diastolic and systolic volumes in the heart. Additionally, the heart no longer has a large area of non-contracting muscle, and the rest of the heart can now pump better and more efficiently. The net result is that the cardiac function of the heart is improved, and this improvement can be measured by a reduction is volume and an increase in ejection fraction (the fraction of blood that is pumped out of the heart during each stroke).

Figure 20:
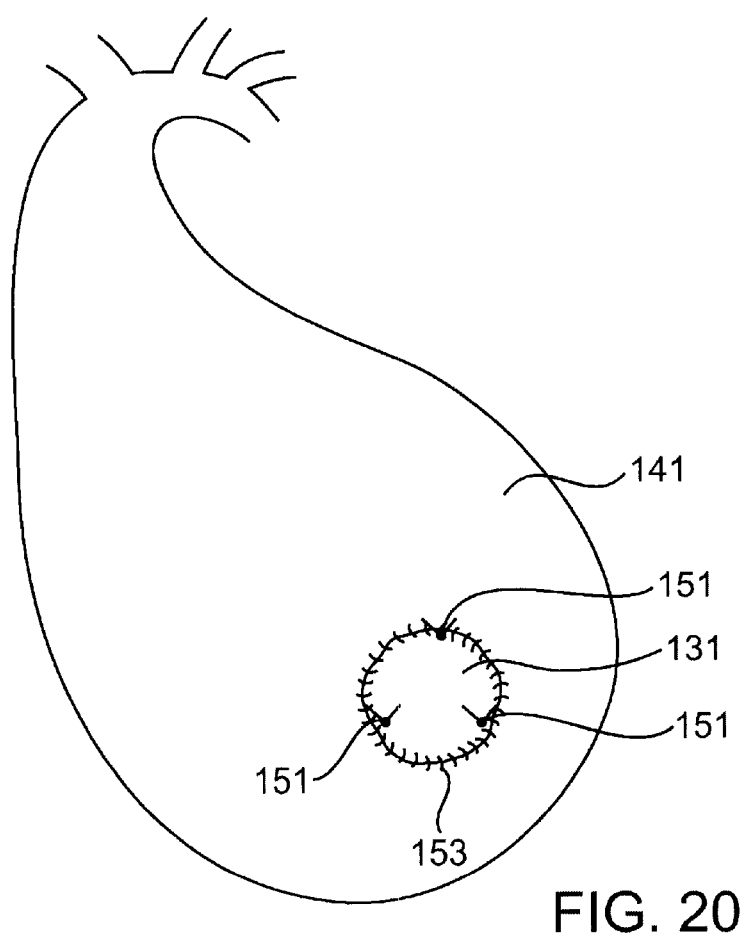
FIG. 20 is a schematic view of the infarcted heart of FIG. 18 after heat treatment and placement of the restraint.

A restraint is then placed over the treated scar tissue. The restraint is trimmed to the appropriate size and shape of the infarct scar. The restraint is then sutured over the infarct zone to prevent expansion of treated site. The restraint is tacked with at least three sutures 151 (see FIG. 20). The sutures are placed just within infarct zone to avoid injuring uninvolved myocardium and at least 3 mm into material to prevent sutures tearing loose. The restraint is drawn as taut as practical and the perimeter of restraint is secured with a running suture line 153 between the tack sutures. The sutures are placed no greater than 3 mm apart. The suturing is preferably performed at the beginning of diastole (minimal pressure and volume) to ensure tightest fit of the restraint. The surgery is then completed in the customary manner.

EXAMPLE 1

Adult female Sprague-Dawley rats are anesthetized, intubated, ventilated, and the chest incised. The left main coronary artery is visualized and ligated. The chest and skin is closed. This procedure created a large myocardial infarction over the left ventricle of the heart.

After 6 weeks, the rats received echocardiography to determine the extent of the infarcted area, to measure the diastolic area, measure the systolic area, and to measure the fractional shortening of the heart. (Fractional shortening is similar to ejection fraction, however ejection fraction measure the volume of blood ejected during each stroke and the fractional shortening measures the change in linear distance between the walls of the left ventricle. Fractional shortening is used in many animal experiments to assess cardiac function.)

The rats are then anesthetized, intubated, and ventilated and the chest opened. The infarct scar is visualized and sutures are placed around the infarct scar. The distances between the sutures are measured. A heating device is placed on the infarct scar. The heating device has two electrodes where each electrode has a length of 2 mm, a width of 1 mm and the space between the electrode is about 1.5 mm. Each electrode has a temperature sensor in the center of the electrode and the controller controls the RF power such that neither temperature sensor will sense a temperature greater than 85 degrees. A maximum of 5 watts are delivered to the electrodes.

Once the heating device was in place in the center of the infarct scar, RF energy is delivered to the electrodes for 30 seconds. After about 15 seconds of RF delivery, the infarct scar starts to shrink, and after about 20 seconds a steady states is reached. If the scar was large enough, the treatments are repeated on areas of the scar adjacent to the treated areas. After the treatment the scar would be about half its original size. The distance between the sutures are measured again and the incisions are closed.

After the surgery echocardiography is repeated to measure the diastolic area, the systolic area, and the fractional shortening. The results showed that the distance between the sutures reduced up to a maximum of 50%. The diastolic and systolic areas were significantly reduced. The fractional shortening improved up to about 50%. Long term follow up echocardiography is repeated which demonstrated dilation of the treatment area with little difference from control animals.

EXAMPLE 2

Adult female Sheep are anesthetized, intubated, ventilated, and the chest incised. The left descending coronary artery is visualized and ligated about ⅓ up from the apex to the base of the heart. Diagonal branches are also ligated about ⅓ up from the apex to the base of the heart. The chest and skin is closed. This procedure created a large myocardial infarction over the left ventricle at the apex of the heart.

After about 12 weeks, the sheep received echocardiography to determine the extent of the infarcted area, to measure the diastolic volume, measure the systolic volume, and to measure the ejection fraction heart.

The sheep are then anesthetized, intubated, and ventilated and the chest opened. The infarct scar is visualized and piezo-electric crystals are placed around the infarct scar. The crystals are from Sonometrics Corporation London Canada and a Digital Sonomicrometer from the same company is used to analyze the distances between the crystals. A heating device is then placed on the infarct scar. The heating device has two electrodes where each electrode has a length of 8 mm, a width of 4 mm and the space between the electrode is about 5 mm. The heating element has a temperature sensor located between the electrodes that protrudes 1 mm from the bottom surface of the heating element. The temperature sensor has a sharp point which is inserted into the infarct scar tissue and helps to keep the heating element stable and on the same location of the heart. The temperature sensor is used by the controller to control the RF power such that the temperature sensor will sense a temperature of the tissue no greater than 95 degrees. A maximum of 20 watts are delivered to the electrodes.

Once the heating device was in place in the center of the infarct scar, RF energy is delivered to the electrodes for 30 seconds. After about 15 seconds of RF delivery, the infarct scar starts to shrink, and after about 20 seconds a steady states is reached. The treatments are repeated on areas of the scar adjacent to the treated areas in a spirally outward tiling pattern to treat the entire scar. Up to 30 treatments are used to treat the entire scar. After the treatments the scar would be about half its original size.

A restraint is then placed over the treatment area to keep the hearts from dilating. The restraint is secured using three tack sutures into the edge of the infarcted area and a running suture between the tack sutures.

After the surgery the distance between the crystals is analyzed and echocardiography is repeated to measure the diastolic volume, the systolic volume, and the ejection fraction. The results showed that the distance between the crystals reduced, the diastolic volume reduce, the systolic volume reduced and the ejection fraction increased up to about 50%. At ten weeks post surgery the measurements are repeated and demonstrate continued benefit from the heat treatment.

While several particular embodiments of the invention have been illustrated and described, it will be apparent that various modifications can be made without departing from the spirit and scope of the invention. Accordingly, it is not intended that the invention be limited except as by the issued claims that ultimately come from this application.

What is claimed is:
1. A device for heating organs or tissue comprising:
(a) an electric cable with proximal and distal ends;
(b) a handle with proximal and distal ends with the proximal end connected to the distal end of the cable;
(c) a stem with proximal and distal ends with the proximal end of the stem connected to the distal end of the handle;
(d) a heating element with a first surface for contacting the organ or tissue, the heating element connected to the distal end of the stem wherein the heating element comprises at least two electrodes and only one temperature sensor positioned on the first surface for sensing a temperature of the organ or tissue adjacent to the sensor, wherein the sensor is located about half-way between the electrodes;

(e) a radio frequency energy source connected to the electrodes via the electric cable; and (f) a regulator connected to the energy source and the temperature sensor of the organ or tissue, for controlling the temperature of the organ or tissue from about 60 degrees C. to about 99 degrees C.

2. The heating device of claim 1 wherein the temperature sensor has a sharp pointed tip which protrudes from the first surface of the heating element from about 0.1 to 10 mm.

3. The heating device of claim 2 wherein the temperature sensor protrudes from the first surface of the heating element from about 0.5 mm to about 5 mm.

4. The heating device of claim 3 wherein the temperature sensor protrudes from the first surface of the heating element about 1.25 mm.

5. The heating device of claim 1 wherein the at least two electrodes are sized and spaced to create a heat treatment zone of at least 8 mm in width.

6. The heating device of claim 1 wherein the at least two electrodes are sized and spaced to create a heat treatment zone of about 1 to about 3 mm deep.

7. The heating device of claim 1 wherein the at least two electrodes are sized and spaced to create a heat treatment zone of about 70 to about 250 square mm.

8. A device for heating organs or tissue comprising:

(a) an electric cable with proximal and distal ends;

(b) a handle with proximal and distal ends with the proximal end connected to the distal end of the cable;

(c) a stem with proximal and distal ends with the proximal end of the stem connected to the distal end of the handle;

(d) a heating element with a first surface for contacting the organ or tissue connected to the distal end of the stem wherein the heating element comprises two electrodes and at least one temperature sensor positioned on the first surface for sensing a temperature of the organ or tissue adjacent to the sensor, wherein the electrodes have a length L, a width W and are separated by a space S wherein the space S is less than the length L and no greater than 10 mm, the width W of the electrodes is greater than 0.2 times the space S and equal or less than the length L;

(e) a radio frequency energy source connected to the electrodes via the electric cable; and (f) a regulator connected to the energy source and the temperature sensor of the infarct scar tissue, for controlling the temperature of the organ or tissue from about 60 degrees C. to about 99 degrees C.

9. The heating device of claim 8 wherein the space S ranges from about 0.3 L to about 1 L.

10. The heating device of claim 9 wherein the space S is about 0.625 L.

11. The heating device of claim 8 wherein the space S is less than 6 mm.

12. The heating device of claim 8 wherein the space S is less than 3 mm.

13. The heating device of claim 8 wherein the width W ranges from about 0.2 S to about 2 S.

14. The heating device of claim 13 wherein the width W ranges from about 0.33 S to about 1 S.

15. The heating device of claim 14 wherein the width W is 0.8 S.

16. The heating device of claim 8 wherein the width W ranges from about 0.2 L to about 1 L.

17. The heating device of claim 16 wherein the width W ranges from about 0.33 L to about 0.67 L.

18. The heating device of claim 17 wherein the width W is 0.5 L.

19. The heating device of claim 8 wherein the width W is 4 mm, the length L is 8, and the space S is 5 mm.

20. The heating device of claim 8 wherein the handle, the stem, and the heating element form a non-catheter based cardiac surgery instrument.

21. The heating device of claim 20 wherein the handle and stem are configured to deliver the heating element to an exterior surface of the heart.

22. The heating device of claim 8 wherein the length L is about 8 mm or less.

23. The heating device of claim 8 wherein the at least two electrodes are sized and spaced to create a heat treatment zone of at least 8 mm in width.

24. The heating device of claim 8 wherein the at least two electrodes are sized and spaced to create a heat treatment zone of about 1 to about 3 mm deep.

25. The heating device of claim 8 wherein the at least two electrodes are sized and spaced to create a heat treatment zone of about 70 to about 250 square mm.

26. A device for heating organs or tissue comprising:

(a) a heating element with a first surface for contacting the organ or tissue wherein said heating element comprises at least two electrodes having a length L which are separated by a distance S no greater than 10 mm and at least one temperature sensor protruding from the first surface, wherein the distance S ranges from about 0.3 L to about 1 L;

(b) means for delivering radio frequency energy to the heating element;

(c) a radio frequency energy source connected to said means; and (d) means for regulating the temperature of the heating element.

27. The heating device of claim 26 wherein there is only one temperature sensor and the sensor is located about half-way between the electrodes.

28. The heating device of claim 27 wherein the temperature sensor has a sharp pointed tip which protrudes from the first surface of the heating element from about 0.1 mm to about 10 mm.

29. The heating device of claim 28 wherein the temperature sensor protrudes from the first surface of the heating element from about 0.5 mm to about 5 mm.

30. The heating device of claim 29 wherein the temperature sensor protrudes from the first surface of the heating element about 1.25 mm.

31. The heating device of claim 26 wherein the heat delivering member is positioned on a non-catheter based cardiac surgery instrument.

32. The heating device of claim 26 wherein the at least two electrodes are sized and spaced to create a heat treatment zone of at least 8 mm in width.

33. The heating device of claim 26 wherein the at least two electrodes are sized and spaced to create a heat treatment zone of about 1 to about 3 mm deep.

34. The heating device of claim 26 wherein the at least two electrodes have a length L of about 8 mm or less.

35. A device for heating organs or tissue comprising:

(a) a heating element with a first surface for contacting the organ or tissue wherein said heating element comprises at least two electrodes separated by a distance no greater than 10 mm and at least one temperature sensor protruding from the first surface, wherein the heating element has a plurality of grooves on its first surface;

(b) means for delivering radio frequency energy to the heating element;

(c) a radio frequency energy source connected to said means; and (d) means for regulating the temperature of the heating element.

36. A device for heating organs or tissue comprising:

(a) an electric cable with proximal and distal ends;

(b) a handle with proximal and distal ends with the proximal end connected to the distal end of the cable;

(c) a stem with proximal and distal ends with the proximal end of the stem connected to the distal end of the handle;

(d) a heating element with a first surface for contacting the organ or tissue, the heating element connected to the distal end of the stem wherein the heating element comprises at least two electrodes and at least one temperature sensor positioned on the first surface for sensing a temperature of the organ or tissue adjacent to the sensor;

(e) a radio frequency energy source connected to the electrodes via the electric cable; and (f) a regulator connected to the energy source and the temperature sensor of the infarct scar tissue, for controlling the temperature of the organs or tissue from about 60 degrees C. to about 99 degrees C., wherein the handle, the stem, and the heating element form a non-catheter based cardiac surgery instrument.

37. The heating device of claim 36 wherein the at least two electrodes are sized and spaced to create a heat treatment zone of at least 8 mm in width.

38. The heating device of claim 36 wherein the at least two electrodes are sized and spaced to create a heat treatment zone of about 1 to about 3 mm deep.

39. The heating device of claim 36 wherein the at least two electrodes have a length L of about 8 mm or less.

40. A device for heating organs or tissue comprising:

(a) an electric cable with proximal and distal ends;

(b) a handle with proximal and distal ends with the proximal end connected to the distal end of the cable;

(c) a stem with proximal and distal ends with the proximal end of the stem connected to the distal end of the handle;

(d) a heating element with a first surface for contacting the organ or tissue, the heating element connected to the distal end of the stem wherein the heating element comprises at least two electrodes and at least one temperature sensor positioned on the first surface for sensing a temperature of the organ or adjacent to the sensor, wherein the at least two electrodes have a length L and a space S between the electrodes which ranges from about 0.3 L to about 1 L;

(e) a radio frequency energy source connected to the electrodes via the electric cable; and (f) a regulator connected to the energy source and the temperature sensor of the infarct scar tissue, for controlling the temperature of the organ or tissue from about 60 degrees C. to about 99 degrees C.

41. The heating device of claim of 40 wherein the at least two electrodes have a length L which is about 8 mm or less.

* * * * *